United States Patent
Nuopponen et al.

(10) Patent No.: US 10,144,007 B2
(45) Date of Patent: Dec. 4, 2018

(54) METHOD FOR RECOVERING CATALYST

(71) Applicant: UPM-Kymmene Corporation, Helsinki (FI)

(72) Inventors: Markus Nuopponen, Helsinki (FI); Lauri Kuutti, Espoo (FI); Stella Rovio, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 218 days.

(21) Appl. No.: 15/038,190

(22) PCT Filed: Dec. 9, 2014

(86) PCT No.: PCT/FI2014/050971
§ 371 (c)(1),
(2) Date: May 20, 2016

(87) PCT Pub. No.: WO2015/086901
PCT Pub. Date: Jun. 18, 2015

(65) Prior Publication Data
US 2016/0288115 A1    Oct. 6, 2016

(30) Foreign Application Priority Data
Dec. 11, 2013 (FI) ........................ 20136248

(51) Int. Cl.
*B01J 20/22* (2006.01)
*B01J 20/28* (2006.01)
(Continued)

(52) U.S. Cl.
CPC ........... *B01J 38/52* (2013.01); *B01D 11/0288* (2013.01); *B01D 15/08* (2013.01); *B01J 20/22* (2013.01);
(Continued)

(58) Field of Classification Search
CPC . B01J 38/52; B01J 20/291; B01J 20/22; B01J 20/28016; B01J 20/28047;
(Continued)

(56) References Cited

U.S. PATENT DOCUMENTS

| | | | |
|---|---|---|---|
| 4,061,807 A * | 12/1977 | Shaler | B01D 53/02 210/502.1 |
| 4,202,797 A * | 5/1980 | Jones | B01J 23/92 502/12 |

(Continued)

FOREIGN PATENT DOCUMENTS

| | | |
|---|---|---|
| CN | 103285922 A | 9/2013 |
| JP | 2008120633 | 5/2008 |

(Continued)

OTHER PUBLICATIONS

Anelli, et al., "Fast and Selective Oxidation of Primary Alcohols to Aldehydes or to Carboxylic Acids and of Secondary Alcohols to Ketones Mediated by Oxoammonium Salts under Two-Phase Conditions" J. Org. Chem. 1987, vol. 52, pp. 2559-2562.
(Continued)

*Primary Examiner* — Joseph W Drodge
(74) *Attorney, Agent, or Firm* — Cantor Colburn LLP

(57) ABSTRACT

A catalyst is recovered from an aqueous reaction mixture comprising heterocyclic nitroxyl catalyst and oxidized cellulose, by: —separating the oxidized cellulose from the reaction mixture, —contacting the reaction mixture with solid hydrophobic adsorbent particles with particle sizes below 350, preferably below 200 μm, more preferably below 100 μm, said particles being silica particles provided with functionalized hydrophobicity, —adsorbing the catalyst to the hydrophobic adsorbent particles, and —eluting the catalyst from the adsorbent particles with an organic solvent.

12 Claims, 1 Drawing Sheet

(51) Int. Cl.
| | |
|---|---|
| B01J 31/02 | (2006.01) |
| B01J 38/52 | (2006.01) |
| B01D 11/02 | (2006.01) |
| B01D 15/08 | (2006.01) |
| C07B 63/00 | (2006.01) |
| D21C 11/00 | (2006.01) |
| C07D 211/94 | (2006.01) |
| B01J 20/287 | (2006.01) |
| B01J 20/291 | (2006.01) |
| B01J 31/40 | (2006.01) |

(52) U.S. Cl.
CPC ....... *B01J 20/287* (2013.01); *B01J 20/28016* (2013.01); *B01J 20/28047* (2013.01); *B01J 20/291* (2013.01); *B01J 31/0271* (2013.01); *B01J 31/40* (2013.01); *C07B 63/00* (2013.01); *C07D 211/94* (2013.01); *D21C 11/0085* (2013.01); *B01J 2220/80* (2013.01); *Y02P 20/582* (2015.11)

(58) Field of Classification Search
CPC ...... B01J 20/287; B01J 31/0271; B01J 31/40; B01J 2220/80; B01J 38/48; B01J 38/50; B01J 20/10; B01J 20/103; B01J 20/28; B01J 20/28004; B01J 20/28007; B01J 31/0234; B01J 31/0235; B01D 2231/70; B01D 15/08; B01D 15/424; B01D 15/426; B01D 11/02; B01D 11/028; B01D 11/0288; C07B 63/00; C07B 33/00; C07D 211/94; Y02P 20/582; Y02P 20/584; Y02P 20/586; Y02P 20/588; D21C 3/00; D21C 3/0037; D21C 3/22; D21C 9/00; D21C 11/00; D21C 11/0085
USPC ....... 127/34; 210/638, 656, 805; 502/20, 22, 502/29, 33, 407; 536/56, 57, 127
See application file for complete search history.

(56) References Cited

U.S. PATENT DOCUMENTS

| | | | | |
|---|---|---|---|---|
| 5,624,875 | A * | 4/1997 | Nakanishi | B01J 20/103 501/12 |
| 5,831,043 | A * | 11/1998 | Fleche | C07C 51/29 536/123.12 |
| 6,540,876 | B1 * | 4/2003 | Cimecioglu | C08B 15/02 162/168.3 |
| 9,410,285 | B2 * | 8/2016 | Vuorinen | C08B 15/04 |
| 2003/0051834 | A1 * | 3/2003 | Weerawarna | C08B 15/04 162/9 |
| 2005/0023212 | A1 * | 2/2005 | Inoue | B01J 20/28014 210/502.1 |
| 2011/0077393 | A1 * | 3/2011 | Hammond | B01J 20/103 536/127 |
| 2011/0098464 | A1 * | 4/2011 | Buchanan | A61K 9/2054 536/65 |
| 2014/0110070 | A1 * | 4/2014 | Vuorinen | C08B 15/04 162/60 |
| 2014/0309343 | A1 * | 10/2014 | Venema | B01J 2/00 524/71 |
| 2015/0216783 | A1 * | 8/2015 | Colver | C08B 15/02 424/499 |
| 2015/0322171 | A1 * | 11/2015 | Tienvieri | C08B 15/04 428/401 |
| 2016/0160440 | A1 * | 6/2016 | Paakkonen | C08B 15/02 162/9 |

FOREIGN PATENT DOCUMENTS

| | | |
|---|---|---|
| JP | 2009242590 A | 10/2009 |
| JP | 2010235454 A | 10/2010 |
| JP | 2011116865 A | 6/2011 |
| JP | 2011116866 A | 6/2011 |
| WO | 9507303 A1 | 3/1995 |
| WO | 9947258 A1 | 9/1999 |
| WO | 02059064 A1 | 8/2002 |
| WO | 2005058818 A1 | 6/2005 |
| WO | 2005058851 A1 | 6/2005 |
| WO | 2010116794 A1 | 10/2010 |
| WO | 2013039070 A1 | 3/2013 |

OTHER PUBLICATIONS

Ciriminna, et al., "Industrial Oxidations with Organocatalyst TEMPO and its Derivatives" Organic Process Research & Development 2010, vol. 14, pp. 245-251.

International Search Report dated Feb. 17, 2015; International Application No. PCT/FI2014/050971; International Filing Date Dec. 9, 2014 (3 pages).

Saito, et al., "Cellulose Nanofibers Prepared by TEMPO-Mediated Oxidation of Native Cellulose" Biomacromolecules 2007, vol. 8, pp. 2485-2491.

Anonymous, Silica Gel 60 (0.040-0.063 mm) product brochure, obtained from http://www.merckmillipore.com/FI/en/product/Silica-gel-60-%280.040-063-mm%29,MDA_CHEM-109385, downloaded Jun. 27, 2014 (2 pages).

Written Opinion dated Feb. 17, 2015; International Application No. PCT/FI2014/050971; International Filing date Dec. 9, 2014 (5 pages).

Zhao, et al., Oxidation of Primary Alcohols to Carboxylic Acids With Sodium Chlorite Catalyzed by TEMPO and Bleach: 4-Methoxyphenylacetic Acid (Benzeneacetic acid, 4-methoxy-),Organic Syntheses,vol. 81, p. 195-203 (2005); Coll. vol. 11, p. 107-113 (2009).

* cited by examiner

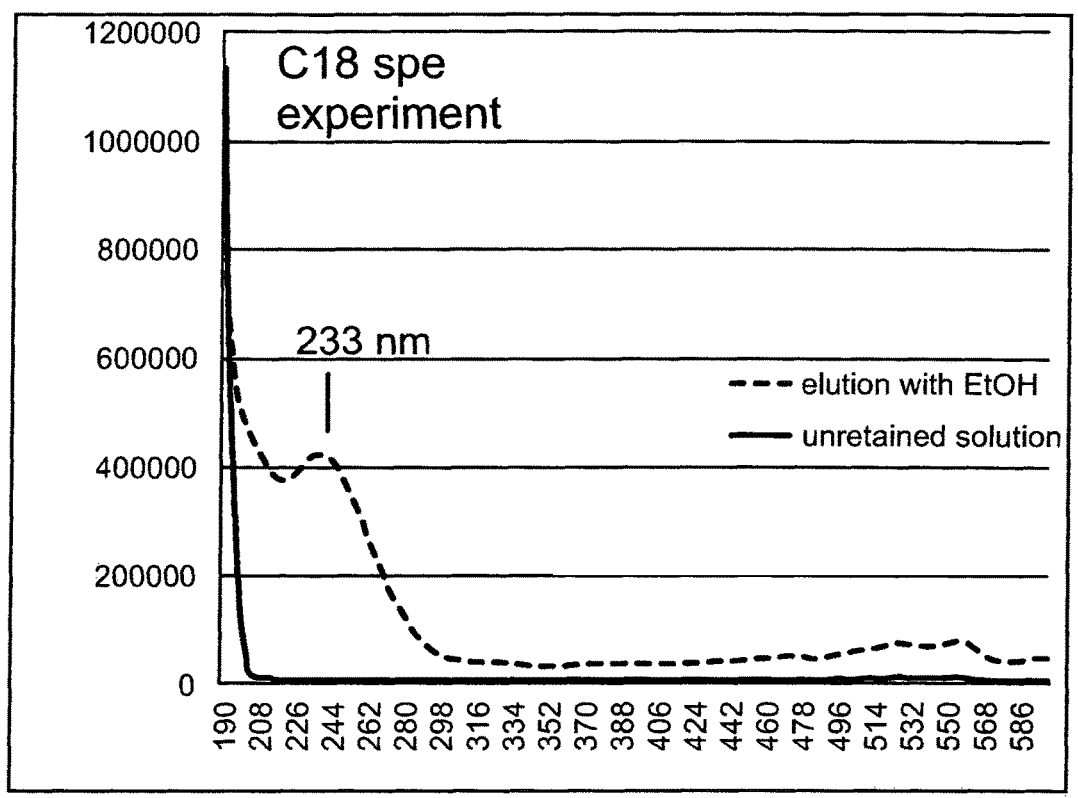
Sample: 25 mg TEMPO - 4.8 g NaCl in 0.2 l H20
Sample volume: 5 ml
EtOH elution volume: 1 ml

US 10,144,007 B2

METHOD FOR RECOVERING CATALYST

CROSS-REFERENCE TO RELATED APPLICATIONS

This application is a National Stage application of PCT/FI2014/050971, filed Dec. 9, 2014 which claims benefit of Finnish Application No. 20136248, filed Dec. 11, 2013, both of which are incorporated by reference herein in their entirety.

FIELD OF THE INVENTION

The invention relates to a method for recovering catalyst.

BACKGROUND OF THE INVENTION

It is known to convert polysaccharides to chemical derivatives by reactions performed on their monomeric units and to impart in this way desired properties to the polymer through altered chemical structure, for example by adding functional groups to the polymer molecule. Cellulose, which is an abundant renewable natural substance, is one example of a polymer that can be converted to many chemical derivatives. The derivatization takes place mostly by chemical reactions of the hydroxyl groups in the β-D-glucopyranose units of the polymer. By chemical derivatization the properties of the cellulose can be altered in comparison to the original chemical form while retaining the polymeric structure.

Heterocyclic nitroxyl compounds are known as catalysts that participate in the selective oxidation of C-6 hydroxyl groups of cellulose molecules to aldehydes and carboxylic acids, the corresponding oxoammonium salt being known as the active direct oxidant in the reaction series. One of these chemical oxidation catalysts known for a long time is "TEMPO", i.e. 2,2,6,6-tetramethylpiperidinyl-1-oxy free radical. Thus, the oxidized forms of the nitroxyl radicals, N-oxoammoniumions, act as direct oxidants in the oxidation of the target cellulose molecule, whereas a main oxidant is used to bring oxygen to the reaction chain and to convert the nitroxyl compound back to the oxidized form.

It is known to oxidize primary alcohols to aldehydes and carboxylic acids through "TEMPO" by using sodium hypochlorite as the main oxidant (for example Anelli, P. L.; Biffi, C.; Montanan, F.; Quici, S.; *J. Org. Chem.* 1987, 52, 2559). To improve the yield in the oxidation of the alcohols to carboxylic acids, a mixture of sodium hypochlorite and sodium chlorite was also used (Zhao, M. M.; Li, J.; Mano, E.; Song, Z. J.; Tschaen, D. M.; *Org. Synth.* 2005, 81, 195).

It is also known procedure to catalytically oxidize cellulose in native cellulose fibers through "TEMPO" by using sodium hypochlorite as main oxidant (oxygen source) and sodium bromide as activator (Saito, T. et al.; Cellulose Nanofibers Prepared by TEMPO-Mediated Oxidation of Native Cellulose, *Biomacromolecules* 2007, 8, 2485-2491). The primary hydroxyl groups (C6-hydroxyl groups) of the cellulosic β-D-glucopyranose units are selectively oxidized to carboxylic groups. Some aldehyde groups are also formed from the primary hydroxyl groups. When the fibers of oxidized cellulose so obtained are disintegrated in water by applying sufficient mechanical energy, they give stable transparent dispersion of individualized cellulose fibrils of 3-5 nm in width, that is, so-called nanofibrillar cellulose.

The catalysts used in the method are expensive, but they do not change irreversibly in the reaction. Therefore, many methods are used for recovering the heterocyclic nitroxyl catalyst such as "TEMPO" from reaction mixtures after the completion of the reaction so that it could be reused. At the same time the toxic catalyst is removed from the reaction mixture which can, after possible other purification steps, be discharged as effluent.

Methods that have been used include distillation of reaction mixture filtrate and recovery of the catalyst as distillate (JP2011116865), solvent extraction of reaction mixture with an organic solvent immiscible with water (JP2011116866), addition of adsorbent to the reaction mixture and recovery of the catalyst from the adsorbent or addition of ion exchange resin to adsorb by-products (JP2009242590), extraction of the reaction mixture with supercritical $CO_2$ (JP2010235454), or desalting the reaction mixture by electrophoresis (WO10116794).

Publication WO2005/058851 discloses a process of separation of heterocyclic nitroxyl catalyst from an acidic aqueous medium with a cation exchange resin. After being adsorbed on the cation exchange resin, the heterocyclic nitroxyl catalyst, which is in nitrosonium and/or hydroxylamine form, can be washed off or eluted.

Publication WO2005/058818 discloses separating the heterocyclic nitroxyl catalyst remaining in the reaction mixture by contacting the reaction mixture with a hydrophobic resin and removing the catalyst from the resin by eluting it with an organic solvent or a mixture of water and a water-miscible organic solvent. The heterocyclic nitroxyl catalyst is separated from the organic solvent or mixture of water and a water-miscible organic solvent by adjusting the pH of said solution to value below 4 and removing the organic solvent to obtain a residue containing the catalyst in the nitrosonium and protonated hydroxylamine form, which are non-volatile. It is preferred that the surface area of the hydrophobic resin that is used in the separation is above 380 $m^2/g$ and the porosity is above 0.5 ml/ml. Suitable types mentioned are resins available under tradename XAD, for example XAD-2, XAD-4, XAD-8, XAD-11, XAD-16, XAD-16, XAD-30, or XAD-1180.

The main problem in recovering the heterocyclic nitroxyl catalyst is that it has to be recovered from a large volume of reaction mixture, where it exists at a concentration of below 0.1%, even below 0.05%. Thus, recovery of the catalyst in concentrated reusable form with a good yield is important. If adsorbent is used, it is important to be able to extract the catalyst at a sufficiently high concentration from the adsorbent.

SUMMARY OF THE INVENTION

The purpose of the invention is to provide a new method for removing the used heterocyclic nitroxyl catalyst from the reaction mixture of cellulose oxidation in an effective way, which yields the catalyst in reusable form.

The method comprises contacting the reaction mixture with solid hydrophobic adsorbent particles with particle sizes below 350, preferably below 200 μm, more preferably below 100 μm and with functionalized hydrophobicity. After the catalyst is adsorbed from the reaction mixture to the adsorbent particles, the catalyst is eluted from the adsorbent particles with an organic solvent, to which the adsorbed catalyst has more affinity and whose volume is considerably smaller than the original volume of the original reaction mixture from where the catalyst was adsorbed. The enrichment factor of the catalyst in the separation is very high.

The recovery method of the heterocyclic nitroxyl catalyst from the reaction mixture is solid phase extraction (SPE), which is based on hydrophobic interactions between the organic heterocyclic nitroxyl compound and the non-polar solid adsorbent, which is in form of small particles. The surfaces of the particles are functionalized chemically so that they are hydrophobic. Chromatographically the recovery method is reversed-phase chromatography (RPC), in which the mobile phase (reaction mixture) is significantly more polar than the stationary phase (the adsorbent particles). Thus, the hydrophobic catalyst dissolved in the reaction mixture tends to adsorb to the hydrophobic stationary phase, whereas hydrophilic compounds (especially salts) dissolved in the reaction mixture tend to elute first.

The heterocyclic nitroxyl compound has affinity to hydrophobic adsorbent, and the compound is enriched from the aqueous reaction mixture to the surface of the adsorbent particles. The dissolved salts are not retained by the adsorbent, but are retained in the reaction mixture.

The method is preferably performed by introducing the reaction mixture through a packed column of the solid adsorbent. The ratio adsorbent/reaction mixture is chosen according to the capacity of the adsorbent. Since the particle size of the adsorbent is very small, the adsorbent has large hydrophobic surface available per mass unit of the adsorbent. The heterocyclic nitroxyl compound is eluted from the adsorbent particles by introducing a small volume of organic solvent, preferably an alcohol such as methanol or ethanol, THF or acetone, through the packed column. The organic solvent used is preferably water-soluble.

The small particle size makes the particles to distribute more evenly to a packed column, creating throughflow conditions in the column that enable a good contact of the reaction mixture with the adsorbent particles.

The adsorbent particles are of small size (below 350 μm, preferably below 200 μm and more preferably below 100 μm), and their surfaces are made hydrophobic by functional groups (functionalized hydrophobicity). The material of the particles is thus chosen according to the possibility of making miniature particles, whereas the hydrophobicity is made separately on the particles. The particle size is so-called e.s.d. (equivalent spherical diameter), the diameter of a sphere having equal volume.

The hydrophibicity of the particles is accomplished by linking hydrophobic carbon chains of suitable length to the particle (carbon-chained functionalized hydrophobicity). For example C6-C18 chains can be used. These chains are alkyl chains with corresponding number of carbon atoms. Thus, notion "C18" stands for octadecyl carbon chain-bonded particle.

Suitable adsorbent particles include especially silica-based particles with carbon-chain functionalized hydrophobicity on their surfaces (for example C-18, C-8 and C-6-functionalized).

Carbon-chain functionalized silica-based particles, especially C-16-C-18 functionalized, are preferred adsorbent particles.

The heterocyclic nitroxyl catalyst is used in the catalytic oxidation process of cellulose, where the cellulose is oxidized at C-6 carbons to carboxyl groups through the catalyst using a main oxidant, which provides the oxygen for the reaction and whose amount in relation to the amount of cellulose can be used to adjust the degree of conversion of the cellulose. Hypochlorite, such as sodium hypochlorite, can be used as the main oxidant. The catalyst is recovered from this reaction mixture after the completion of the reaction using the method, and it can be then be reused in a similar catalytic oxidation process.

The oxidized cellulose obtained after the catalytic oxidation process can be processed to a final cellulose product.

When the starting material is pulp derived from plants, especially wood, the cellulose exists in fiber form. The fibers that contain the cellulose in oxidized form as a result of the oxidation process are easy to disintegrate by mechanical methods to small-scaled fragments, nanofibrillar cellulose (NFC).

The oxidized cellulose is separated from the reaction mixture by a suitable solid-liquid separation method, such as filtration. The remaining reaction mixture, which contains the catalyst to be recovered and salts (mainly chloride if hypochlorite was used as oxidant, and possibly bromide if bromide has been used as cocatalyst), may still contain dispersed colloidal matter which must be removed from the mixture so that it does not disturb the adsorption of the catalyst to the adsorbent particles.

Wash water of the separated oxidized cellulose also contains amounts of the catalyst and it can be combined to the reaction mixture before the recovery of the catalyst.

BRIEF DESCRIPTION OF THE DRAWINGS

In the following, the invention will be described with reference to the appended drawings, where FIG. 1 illustrates the recovery of the catalyst in example 1.

DETAILED DESCRIPTION OF THE PREFERRED EMBODIMENTS

In the following disclosure, all percent values are by weight, if not indicated otherwise. Further, all numerical ranges given include the upper and lower values of the ranges, if not indicated otherwise.

In the present application all results shown and calculations made, whenever they are related to the amount of pulp, are made on the basis of dried pulp.

General Description of Catalytic Oxidation and Catalyst

In the invention, the catalyst to be recovered is the result of a catalytic oxidation process where primary hydroxyl groups of cellulose are oxidized catalytically by a heterocyclic nitroxyl compound, for example 2,2,6,6-tetramethyl-piperidinyl-1-oxy free radical, "TEMPO". Other heterocyclic nitroxyl compounds known to have selectivity in the oxidation of the hydroxyl groups of C-6 carbon of the glucose units of the cellulose can also be used, and these compounds are widely cited in the literature. Hereinafter, the oxidation of cellulose refers to the oxidation of these hydroxyl groups to aldehydes and/or carboxyl groups.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C-6 carbon in cellulose after it has been activated. Other known members of this group are the TEMPO derivatives 4-methoxy-TEMPO and 4-acetamido-TEMPO.

In this disclosure, catalytic oxidation refers to nitroxyl-mediated (such as "TEMPO"-mediated) oxidation of hydroxyl groups. The catalytic oxidation of fibers or fibrous material in turn refers to material which contains cellulose that is oxidized by nitroxyl-mediated (such as "TEMPO"-mediated) oxidation of hydroxyl groups of the cellulose.

The heterocyclic nitroxyl compound used as catalyst in the oxidation process (such as "TEMPO") is stable in its neutral, radical form, and it can be stored in that form. After the catalyst is activated to the oxidized form, it can participate at once in the reaction, and the oxidation process of the cellulose starts quickly.

The structural formula of "TEMPO" in its radical form is given below

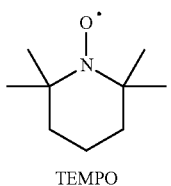

TEMPO

The catalyst can be activated in various ways. After the activation, the oxidation reaction can be started and performed to completion to a desired conversion degree in a reaction medium in the presence of the catalyst, cellulose and main oxidant. The reaction medium can be water-based medium where the materials are dissolved and suspended. In the case of pulp raw material, the cellulose exists in fibre form as suspension in water in a suitable consistency, whereas the catalyst and the main oxidant are dissolved in the water. The pH of the reaction medium is controlled during the reaction to keep it in the optimum range. Temperature of the reaction medium may also be controlled.

Recovery of the Catalyst

After the catalytic oxidation of cellulose, the oxidized cellulose in fibrous from is separated from the reaction mixture. Colloidal suspended matter, which could not be separated together with the fibrous matter, mainly cellulose and hemicellulose, is removed by more accurate separation methods, such as fine filtration of centrifugation.

A clear aqueous reaction mixture containing remaining dissolved matter, including the catalyst, is introduced through a packed column of a solid adsorbent, which consists of particles having surfaces that are hydrophobic through functionalization made on the particle surfaces. The column can be a chromatography column, through which the reaction mixture is pumped so that it flows from the top downwards. In course of the flow through the column, the catalyst, which is in the reduced neutral form, separates as it is retained by the hydrophobic adsorbent to which it has affinity while the dissolved salts travel through the column along with the flow of the aqueous mixture. Visually the separated catalyst can be detected as a coloured zone in the column.

The catalyst is eluted from the adsorbent particles by introducing a small volume of organic solvent, preferably methanol or ethanol, through the packed column. The organic solvent is preferably water-soluble. The catalyst in solid form can be recovered by evaporating the solvent.

The size of the adsorbent particles is below 350 µm, preferably below 200 µm, and more preferably below 100 µm, which makes the surface area of adsorbent in the packed column large with regard to the volume of the packed column. The small particle size is easy to achieve with material that is not inherently hydrophobic. The particles can be made hydrophobic chemically by functionalization, as explained above.

The functionalization is carried out through carbon chains chemically bonded to the surfaces of the particles. Alkyl chains between C6-C18 can be used.

Suitable adsorbent particles include silica-based particles with carbon-chain functionalized hydrophobicity on their surfaces, especially C16-C18 functionalized.

For example with C-18 functionalized silica particles, a separation efficiency above 99.5% (amount of catalyst adsorbed/initial amount of catalyst in the reaction mixture) is achieved. The enrichment factor, which can be calculated as ratio reaction mixture volume/solvent volume, is normally over 30, which means that the liquid volume where the catalyst is dissolved is reduced to less than 1/30 parts of the original, meaning that the concentration of the catalyst is increased over 30-fold, which makes the catalyst reusable in a subsequent catalytic oxidation process of cellulose. The catalyst can be concentrated further by evaporating the solvent, which is easy if the solvent is an organic volatile solvent, such as ethanol, methanol, THF or acetone. Acetone seems to be a good solvent in view of the easiness to remove it by evaporation.

NFC

The heterocyclic nitroxyl catalyst is recovered from and it can be reused in a process for catalytic oxidation of cellulose for the purpose of making nanofibrillar cellulose (NFC). The oxidation process takes place in an aqueous reaction medium containing the cellulose as fibrous raw material, the catalyst, which may have been activated in advance or is activated in the reaction medium, and the main oxidant, preferably hypochlorite.

The fibrous raw material is suspended in the reaction medium can be any fibres consisting mainly of cellulose, especially fibres of plant origin. The fibres, when suspended in the aqueous reaction medium, form a pulp of given consistency. The fibers can be especially from wood. Chemical pulp, such as softwood or hardwood pulp, for example bleached birch pulp, can be used.

The oxidation reaction is allowed to proceed till a required conversion degree (oxidation level) has been achieved. As expressed in carboxylate groups generated as the result of oxidation, this is normally 0.5-1.4 mmol COOH/g pulp.

For the purpose of making NFC, it has been found that the oxidation level (conversion degree) of 0.5-1.1 mmol COOH/g pulp, preferably 0.6-0.95 and most preferably 0.7-0.9 is already sufficient that the cellulose fibers can be easily disintegrated to fibrils by mechanical energy.

After the desired conversion degree has been attained, the reaction medium is taken out from the reactor. The fibres containing the oxidized cellulose are separated from the reaction medium, and the reaction medium is subjected to further purification to remove the colloidal matter before the recovery of the catalyst as explained above.

The fibres are washed to remove the remnants of the chemicals and processed further to NFC.

The term "nanofibrillar cellulose" refers to a collection of isolated cellulose microfibrils or microfibril bundles derived from cellulose raw material. Microfibrils have typically high aspect ratio: the length might exceed one micrometer while the number-average diameter is typically below 200 nm. The diameter of microfibril bundles can also be larger but generally less than 1 µm. The smallest microfibrils are similar to so called elementary fibrils, which are typically 2-12 nm in diameter. The dimensions of the fibrils or fibril bundles are dependent on raw material and disintegration method. The nanofibrillar cellulose may also contain some hemicelluloses; the amount is dependent on the plant source. Mechanical disintegration of the oxidized cellulose raw material is carried out with suitable equipment such as a refiner, grinder, homogenizer, colloider, friction grinder, ultrasound sonicator, fluidizer such as microfluidizer, macrofluidizer or fluidizer-type homogenizer. Fibers containing oxidized cellulose are more easily disintegrated to nanofibrillar cellulose because the carboxylic groups formed in the cellulose weaken the internal bonds of the fiber.

EXAMPLES

The recovery method is described by way of following examples, which shall not be interpreted as limiting the method.

The glass columns were filled with octadecyl silane sorbent (C18 sorbent) with the particle size of 40 μm and nominal porosity of 60 Å. During the packing, the sorbent was wetted with water to ensure dense packing. The C18 sorbent consists of non-polar octadecylsilane-bonded, irregular silica gel (silica) particles.

Example 1 (TEMPO Extraction)

90 liter of process water used in TEMPO oxidation has been first separated by decanter centrifuge to collect the colloidal substances of the oxidation process. The colloidal substances are mainly cellulose and xylans. After the separation the solution has been pumped through C18 column, where the separation of TEMPO molecules from the solution takes place. The separated TEMPO can be seen as symmetrical red zone in the used column.

The extraction is performed with ethanol and the extraction takes place downward. 1.8 liter ethanol is enough to extract the TEMPO from the column and in the extractant was a precipitate. The extractant was distilled with vacuum (33-40 mbar and 16-19° C.). The separation efficiency has been followed by measuring the TEMPO concentration in different solutions. The starting TEMPO concentration was 160 mg/liter in the process solution and after the column treatments the TEMPO concentration in process water was decreased to 0.05 mg/liter. This means that the trapping efficiency is 99.97% of TEMPO to C18 adsorbent material. The TEMPO concentration in ethanol was 7200 mg/liter. The extraction efficiency was 93% and the enrichment factor 90:1.8=50.

Example 2 (TEMPO Extraction)

90 liter of process water used in TEMPO oxidation has been first separated by decanter centrifuge to collect the colloidal substances of the oxidation process. The colloidal substances are mainly cellulose and xylans. After the separation the solution has been pumped through C18 column, where the separation of TEMPO molecules from the solution takes place. The separated TEMPO can be seen as asymmetrical red zone in the used column due to the unwanted flow phenomenon in the column. The extraction is performed with ethanol and the extraction takes place downward. 1.8 liter ethanol was used to extract the TEMPO from the column and the extractant has a precipitate. The TEMPO concentration in ethanol was 5100 mg/liter. In the water/ethanol solution was 4200 mg/liter TEMPO. The extraction efficiency was 93% and the enrichment factor 90:(1.8+1)=34.

Example 3 (TEMPO Extraction)

70 liter of process water used in TEMPO oxidation has been first separated by decanter centrifuge to collect the colloidal substances of the oxidation process. After the separation the solution has been pumped through narrow C18 column (capacity of 886 cm$^3$, 47 cm long, diameter 4.9 cm), where the separation of TEMPO molecules from the solution takes place. The separated TEMPO can be seen as symmetrical red zone in the used column.

The extraction is performed with acetone and the extraction takes place downward in the speed of 90 ml in minute. 1 liter acetone is enough to extract the TEMPO from the column and the extractant contained 11.2 g of TEMPO. The extractant was distilled with vacuum (10-35 mbar and 15-19° C.). The easy distillate fraction was bright up to 54% of the initial volume and from 54 to 90% it got more yellow colour. The separation efficiency has been followed by measuring the TEMPO concentration in different solutions. After distillation of the readily distillable fraction of the acetone, the residue acetone solution containing TEMPO was was evaporated in fume hood under atmospheric temperature and pressure with airflow. The almost dry TEMPO was collected. The recovery of solid TEMPO was 9.1 g, which means 81% recovery field of solid TEMPO. The extraction efficiency was 93% and the enrichment factor 70:1=70.

Example 4 (Oxidation of Pulp)

Activation of radical TEMPO was first carried out. 0.375 g radical TEMPO was weighted and transferred to closed glass bottle. 50 ml of water was added to bottle. 4 ml of NaClO (12.9%) solution was added to TEMPO solution. pH of TEMPO solution was adjusted to 7.5 by 1 M $H_2SO_4$ using pH meter. Solution was mixed strongly until all radical TEMPO was dissolved.

243 g (48 g as dry) never-dried birch pulp was weighted in closed vessel. Activated TEMPO solution was mixed with pulp. Pulp was shifted to Buchi reactor and 819 ml water was mixed with pulp. Temperature of pulp was set to 18° C. 63 ml (12.9%) NaClO was added to reactor by pump while pulp was mixed strongly. The pH was kept under 9 during NaClO addition by controlling pumping speed. Temperature of pulp was lifted to 25° C. after NaClO addition and pH was controlled by titrator (pH 9, 1 M NaOH) until all NaClO was consumed. Active chlorine titration was used to monitor NaClO consumption during oxidation process. Strong mixing was continued until all NaClO was consumed. Pulp was washed with ion changed water after oxidation. Carboxylate content of pulp (conductometric titration) was determined after pulp consistency determination.

Conversion of residual aldehydes to carboxylates by acidic phase oxidation was carried out in the second stage oxidation. 10 g (calculated as dry) of TEMPO oxidized pulp was weighted and shifted to Buchi reactor. Pulp was diluted by 1000 ml of water. 0.6 g $NaClO_2$ and 2 ml DMSO was mixed with pulp solution. pH of solution was adjusted to 3 by 1 M $H_2SO_4$ using pH meter. Temperature of pulp solution was adjusted to 50° C. and solution was mixed 2 hours until oxidation was completed. Pulp was washed with ion-changed water after oxidation. CED-viscosity and carboxylate content of pulp (conductometric titration) was determined after pulp consistency determination.

The following table compares the performance of fresh catalyst (reference) with the performance of recovered and recycled catalyst.

TABLE 1

Oxidation parameters in oxidation with pure fresh TEMPO (reference) and recycled TEMPO (examples 1 and 3)

| Experiment | REF oxidation | recycled TEMPO (E1) | recycled TEMPO (E3) |
|---|---|---|---|
| Reaction time (min) | 154 | 173 | 171 |
| HOCl addition (mmol NaClO/g pulp) | 2.4 | 2.8 | 2.4 |
| TEMPO addition (mmol/g pulp) | 0.05 | 0.05 | 0.045 |
| mmol COOH/g pulp (1st stage oxidation) | 0.87 | 0.82 | 0.91 |
| mmol COOH/g pulp (2nd stage oxidation) | 0.98 | 0.95 | 1.04 |
| Temperature (° C.) | 25 | 25 | 25 |
| pH | 9 | 9 | 9 |

Example 5. Fluidisation

Pulp consistency of the oxidized pulp sample was adjusted to approximately 1.5% by water. Sample was mixed by Turrax 10 min. pH was adjusted to 9 by NaOH and pH meter. Pulp solution was forced by 2000 bar pressure through 200 μm chamber and 100 μm chamber (=1 pass) of fluidizator (Microfluidics M110P). Pulp dispersion formed a gel in fluidization.

The invention claimed is:

1. A method for recovering catalyst from an aqueous reaction mixture comprising heterocyclic nitroxyl catalyst and oxidized cellulose, the method comprising:
   separating the oxidized cellulose from the reaction mixture,
   after the separation of the oxidized cellulose from the reaction mixture, contacting the reaction mixture with solid hydrophobic adsorbent particles with particle sizes below 350 μm, said particles having surfaces made hydrophobic by functional groups,
   adsorbing the catalyst to the hydrophobic adsorbent particles, and
   eluting the catalyst from the adsorbent particles with an organic solvent.

2. The method according to claim 1, wherein the functionalized hydrophobicity is carbon-chain functionalized hydrophobicity.

3. The method according to claim 2, wherein the carbon-chain functionalized hydrophobicity is C6-C18 hydrophobicity.

4. The method according to claim 1, wherein the hydrophobic particles are silica particles with functionalized hydrophobicity.

5. The method according to claim 1, wherein the organic solvent is water soluble.

6. The method according to claim 5, wherein the water-soluble organic solvent is ethanol, methanol or acetone.

7. The method according to claim 1, wherein the reaction mixture is introduced through a column packed with the solid adsorbent particles, whereafter the organic solvent is introduced through the same column.

8. The method according to claim 1, wherein after the separation of the oxidized cellulose, colloidal matter is removed from the reaction mixture before the reaction mixture is contacted with solid hydrophobic adsorbent particles.

9. The method according to claim 1, wherein the recovered catalyst is recycled to catalytic oxidation of cellulose.

10. The method according to claim 1, wherein the oxidized cellulose exists in fibers in the reaction mixture, and the oxidized cellulose is separated from the reaction mixture by separating the fibers from the reaction mixture.

11. The method according to claim 1, wherein the particle sizes of the solid hydrophobic adsorbent particles are below 200 μm.

12. The method according to claim 1, wherein the particle sizes of the solid hydrophobic adsorbent particles are below 100 μm.

* * * * *